(12) United States Patent
Mehta et al.

(10) Patent No.: US 8,853,459 B2
(45) Date of Patent: Oct. 7, 2014

(54) DECOLORIZATION OF AMINES

(75) Inventors: Anil J. Mehta, Lake Jackson, TX (US);
Stephen W. King, League City, TX (US); William C. Hoffman, Decatur, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/876,388

(22) PCT Filed: Sep. 13, 2011

(86) PCT No.: PCT/US2011/051374
§ 371 (c)(1),
(2), (4) Date: Mar. 27, 2013

(87) PCT Pub. No.: WO2012/044456
PCT Pub. Date: Apr. 5, 2012

(65) Prior Publication Data
US 2013/0204044 A1 Aug. 8, 2013

Related U.S. Application Data

(60) Provisional application No. 61/387,707, filed on Sep. 29, 2010.

(51) Int. Cl.
*C07C 209/84* (2006.01)
(52) U.S. Cl.
CPC .................................. *C07C 209/84* (2013.01)
USPC ....................................................... 564/498
(58) Field of Classification Search
CPC .................................................. C07C 209/84
USPC ........................................................... 564/498
See application file for complete search history.

(56) References Cited

U.S. PATENT DOCUMENTS

| 4,454,347 | A | * | 6/1984 | Parham et al. ................ 564/428 |
| 4,731,165 | A | | 3/1988 | Niebruegge et al. |
| 4,737,243 | A | | 4/1988 | Siml et al. |
| 5,331,102 | A | | 7/1994 | Gibson |
| 5,362,914 | A | | 11/1994 | Su |
| 5,364,971 | A | | 11/1994 | Su |
| 5,861,537 | A | | 1/1999 | Shinohara et al. |
| 6,323,371 | B2 | * | 11/2001 | Ruider et al. ................. 564/497 |
| 7,560,594 | B2 | * | 7/2009 | Haese et al. ................... 564/497 |

FOREIGN PATENT DOCUMENTS

| EP | 0 962 448 | 12/1999 |
| GB | 1351050 | 4/1974 |
| JP | 3 281036 | 12/1991 |
| JP | 4 290850 | 10/1992 |

* cited by examiner

*Primary Examiner* — Brian J Davis
(74) *Attorney, Agent, or Firm* — Kagan Binder, PLLC

(57) ABSTRACT

The present invention provides methods that are used to decolorize compositions containing one or more amines in the presence of one or more weak acids. Significantly, the weak acids, particularly organic acids such as glacial acetic acid, when used in combination with a heat treatment produce dramatically less by-products than do the stronger mineral acids, making heat treatments and subsequent separation techniques more effective while producing less waste. In some modes of practice, the weak acids do not need to be neutralized, eliminating neutralizing steps and waste streams associated with neutralization. Low color products can be obtained easily at very high yield as a consequence.

18 Claims, No Drawings

006 US 8,853,459 B2

DECOLORIZATION OF AMINES

PRIORITY CLAIM

The present non-provisional patent application claims benefit from U.S. Provisional patent application having Ser. No. 61/387,707, filed on Sep. 29, 2010, by Mehta et al., and titled DECOLORIZATION OF AMINES, wherein the entirety of said provisional patent application is incorporated herein by reference.

FIELD OF THE INVENTION

The present invention relates to a method of decolorizing compositions that include one or more amines. More particularly, the invention involves preheating the compositions in the presence of at least one weak acid and then recovering low color amine(s) from the heat treated composition.

BACKGROUND OF THE INVENTION

The processes used to manufacture amines tend to produce mixtures of these compounds. These mixtures can be resolved in a variety of ways. For example, distillation can be used to fractionate these mixtures. It is well known that amines such as polyethylene amines become discolored during manufacture and/or during storage in air. The mixtures often are yellow, yellow brown, or dark brown in color. It is believed in the industry that the discoloration is attributable to impurities in the product mixtures. These impurities may be by-products of the process of making the amines. Usually, the commercial value of strongly discolored amines is less than the commercial value of low color amines, often very significantly less. Accordingly, many processes have been devised to decolorize compositions including one or more of these amine compounds.

Strong mineral acids, e.g., those having a pKa of under about 1.0 at 25° C., include hydrogen halides such as HCl, HBr, and HF as well as sulfuric acid, nitric acid, combinations of these, and the like. Strong mineral acids have been used to decolor amines. Each of GB 1351050A, DE 2163516C3, and JP 1970-119902 describes a process of decolorizing polyethyleneamines by vacuum distillation in the presence of their hydrochlorides. The hydrochloride is obtained by adding hydrochloric acid to the amines.

U.S. Pat. No. 5,861,537 (1999) describes a process of decolorizing polyetheyleneamines by treating the amities with hydrogen halides, distilling TETA and lower boiling amines, then neutralizing the excess acid in the residual liquor by adding alkali and then distilling the high-boiling amines from the mixture.

Although hydrogen halides offer a high degree of decolorization, the use of hydrogen halides is quite problematic. Firstly, hydrogen halides tend to be highly corrosive, strong acids. These acids have a strong corrosive effect on equipment unless expensive, corrosion-resistant equipment is used. These acids require careful handling. Further, when reacted with compositions including one or more amines, these acids tend to react with the amines to form amine hydrohalide by-products. For example, if HCl is used, the amine hydrochlorides remain in the bottom of a distillation column when the amine-HCl mixture is distilled for recovering the decolorized amine. The amine hydrochloride must be either disposed of as a low value byproduct, neutralized by adding an aqueous alkali solution to liberate the amine, and/or the like. The byproduct salt and water then need to be separated from the amine product(s). The added HCl can lead to acid-catalyzed amine decomposition if too much acid is added and/or too much heat is added. As little as 1% by weight HCl in amine can decrease the amine decomposition temperature by 50° C., for instance. Therefore, HCl concentration in the amine composition must be tightly controlled. Further, the process disclosed by U.S. Pat. No. 5,861,537 requires heating the mixture to high temperatures (150° C. to 240° C.) for effective decolorization. Often, the existing equipment that is available to be used to reduce color might not be suitable for such high temperature operation. It would be desirable if a method could be used over a wider range of temperatures, e.g., lower temperatures or even higher temperatures, so that a wider range of equipment could be used.

Consequently, there remains a strong demand for methods that decolorize amine mixtures to a high degree without suffering from one or more of these significant drawbacks.

SUMMARY OF THE INVENTION

The present invention provides methods that are used to decolorize compositions containing one or more amines. The methods use acids that are weaker, e.g., pKa of greater than about 1, preferably greater than about 2, more preferably greater than about 3, even more preferably greater than about 4, and significantly that are less corrosive than the strong mineral acids used conventionally. Significantly, the weaker acids, particularly organic acids such as glacial acetic acid, when used in combination with a heat treatment produce dramatically less by-products than do the stronger mineral acids. Acid neutralization and salt separation steps are not required when using weaker acids such as organic acids because the presence of corresponding byproducts of the organic acids in the amine(s) generally is not a concern to the integrity of the product in contrast to the presence of by-product salts such as chlorides. Low color products can be obtained easily at very high yield as a consequence.

It is counterintuitive and surprising that using a heat treatment in combination with one or more weaker acids, particularly one or more organic carboxylic acids, dicarboxylic acids or anhydrides thereof, can be so effective at decoloring amines with low levels of by product formation. Generally, organic acids such as carboxylic acids are reactive with amines. For instance, carboxylic acids tend to react with amines to form amide moieties and water and sometimes imidazoline moieties. Consequently, there would be an expectation that using such acids to treat amines would tend to consume the amines, reducing yield and producing undue amounts of by-products. Yet, the present invention yields a very low level of undesired by-products and exceptionally high yields of decolored amines in a simple process requiring only heat treatment and a subsequent separation, such as distillation.

Further, there would tend to be an expectation that one would have to use greater amounts of a weaker acid relative to a stronger acid in order to achieve an effective degree of decolorization. Yet, using greater amounts of a weaker acid would be expected to lead to more undesired by-product formation in that more weaker acid would be present to react with the amines. Thus, there would be a bias to avoid using a weaker acid such as a carboxylic acid in order to minimize by-product formation and to avoid reducing amine yield. This is indeed the case when a suitable heat treatment is not carried out or unduly high amounts of acid are used instead to compensate for inadequate heat treatment. Yet, the present invention achieves a substantial degree of decolorization when using very low levels of weaker acids in combination with a heat treatment to help avoid undue production of by-products.

It is unexpected that using a heat treatment would allow low levels of weak acids to provide such a high degree of decolorization.

The ability of a heat treatment to enhance the decolorization efficacy of weaker acids is also counterintuitive. Preheating a mixture of amines in the presence of any acid for a significant period of time would be expected to enhance reaction kinetics between the amines and the acid to favor undesired by-product formation. It is counterintuitive that a heat treatment increases the decoloring power of weaker acids without producing undue amounts of by-products as might otherwise be expected.

In one aspect, the present invention relates to a method of reducing the discoloration of a composition including one or more amines and one or more color bodies, comprising the steps of:
  (a) providing the composition, wherein the composition has an initial color;
  (b) heat treating the composition in the presence of at least one weak acid under conditions effective to modify the composition so that a separation technique can more effectively separate at least a portion of the amines from at least a portion of the color bodies; and
  (c) after heat treating, using at least the separation technique to recover at least a portion of the amines from the heat treated composition in a manner such that the recovered portion has less color relative to the initial color.

In another aspect, the present invention relates to a method of reducing the discoloration of a composition including one or more amines, comprising the steps of:
  (a) providing the composition, wherein the composition has an initial color;
  (b) heat treating the composition in the presence of at least one weak acid for a period of at least about 20 minutes; and
  (c) after heat treating, applying at least one separation technique to the heat treated composition to recover at least a portion of the amines from the heat treated composition in a manner such that the recovered portion has a less color relative to the initial color.

In another aspect, the present invention relates to a method of reducing the discoloration of a composition including one or more amines, comprising the steps of:
  (a) providing the composition, wherein the composition has an initial color;
  (b) heat treating the composition in the presence of at least one weak acid for a period of at least about 20 minutes;
  (c) using a color characteristic of the heat treated composition to help determine when heat treating is complete; and
  (d) after heat treating, applying at least one separation technique to the heat treated composition to recover at least a portion of the amines from the heat treated composition in a manner such that the recovered portion has a reduced color relative to the initial color.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides strategies to decolorize compositions including at least one amine. As used herein, the term "amine" refers to an organic compound that includes at least one amine moiety, preferably at least two amine moieties, more preferably at least three amine moieties, and even more preferably at least four amine moieties. Amines that include two or more amine moieties are referred to herein as polyamines. An organic compound as used herein refers to a compound that includes at least one carbon atom and at least one hydrogen atom that is covalently bound to a carbon atom or that is covalently bound to an oxygen atom that is covalently bound to a carbon atom. The amine compounds may be linear, branched, cyclic, or acyclic, saturated, unsaturated, aliphatic, and/or aromatic.

An exemplary class of amines includes hydrocarbyl amines. This kind of amine includes at least one hydrocarbyl moiety and at least two amine moieties. The term "hydrocarbyl" refers to a moiety in which C and H atoms constitute at least 50 weight percent, preferably at least 60 weight percent, more preferably at least 80 weight percent, and even more preferably 100% of the moiety. In addition to C and H, such moieties may include other atoms such as O, covalently bound halogen such as bromo atoms, P, S, combinations of these and the like. Hydroxy-functional alkyl or alkylene moieties are examples of hydrocarbyl moieties including one or more O atoms. The hydrocarbyl moieties independently may be acyclic or cyclic; branched or linear; saturated or unsaturated; aliphatic or aromatic; or combinations of these.

Preferred hydrocarbyl moieties are independently divalent, trivalent, tetravalent, pentavalent, and/or hexavalent alkylene moieties of 1 to 50, preferably 1 to 20, more preferably 1 to 10, and even more preferably 2 to 6 carbon atoms. If other kinds of atoms are present in the alkylene moieties, desirably these are incorporated into moieties that are substantially inert with respect to the process conditions used in the decolorization methods of the present invention.

In many embodiments, polyamines include from 2 to about 20, preferably 2 to about 10, more preferably 4 to about 6 amine moieties. The amine moieties can be primary, secondary, and/or tertiary.

Examples of amines include monoethanolamine (MEA), diethanolamine (DEA), triethanolamine (TEA), ethylene diamine (EDA), 1,3-diaminopropane (1,3-DAP), diethylenetriamine (DETA), triethylenetetramine (TETA), tetraethylenepentamine (TEPA), pentaethylenehexamine (PEHA), piperazine (PIP), aminoethylpiperazine (AEP), h-piperazine (h-PIP), aminoethylethanolamine (AEEA), combinations of these, and the like. Often, a discolored composition includes combinations of these amines in admixture. However, discoloration is most often a problem associated with higher molecular weight amines (e.g., those including at least four amine moieties) as the lower molecular weight amines such as EDA and often DETA often can be obtained in low color by distillation without requiring a heat treatment according to the present invention. In combination or recovered in isolation, many of the amine compounds have more commercial value when decolorized. For example, amine compositions including TETA often in combination with other amines can become strongly discolored when produced and/or when exposed to oxygen in the ambient. APHA color values (see below for a discussion of APHA color) as high as 5000 are common. Yet, TETA and/or congeners of TETA, particularly linear TETA (L-TETA) with low color content (color less than 50 APHA according to some specifications) are in high demand for use in applications such as epoxy hardening agents, fuel additives, and polyamide resins.

Without wishing to be bound, it is believed that the color issue associated with amine compositions is attributable at least in part to the presence of coloring agents (also referred to as color bodies) that are produced as by-products of the process of producing amines. It can be difficult to separate the desired amine products from the coloring agents, even when techniques such as distillation are used. The present invention uses a strategy that is believed to modify the color bodies in a way that makes it much easier to separate the amines from the color bodies. This makes it easier to provide compositions with not only dramatically reduced color but also with substantially less by-products than are formed when using acid halide treatments such as are described in GB 1351050 and U.S. Pat. No. 5,861,537.

The effectiveness of the decolorizing method of the present invention can be quantified by using the Platinum-Cobalt (Pt/Co) color scale (also known as the APHA-Hazen color scale or APHA color scale) using methods according to ASTM D1209-00, "Standard Test Method for Color of Clear Liquids (Platinum-Cobalt Scale)," ASTM International, West Conshohocken, Pa. (2000). Hereinafter, color data obtained using this method shall be referred to as APHA color data. The method originally was developed as a way to evaluate pollution levels in waste water. The use of APHA color methods to assess color has expanded beyond waste water into many other industrial applications. Because discolored amine compositions tend to be yellowish to brown in color, the APHA color methods are applicable and useful to assess the color of amine compositions in the practice of the present invention. Prior to treatment, a discolored amine composition may have an APHA color in the range from about 200 or more, often from about 200 to about 5000, and even from about 400 to about 5000. After only a single cycle of treatment according the present invention, the APHA color is reduced to under 150, and in preferred modes of practice even under 50, even under 20, and even under 10.

The compositions to be subjected to a decolorizing treatment may include water or may be anhydrous. However, recognizing that some water may be produced as a by-product during the decolorizing treatment, it is desirable to limit or even avoid the presence of water in the composition as initially presented for treatment. This reduces the need to remove water from the decolorized product and a possible loss of product while removing the water. This is advantageous, because many commercial specifications for the amines generally specify essentially anhydrous amines. Accordingly, the decolorizing treatment of the present invention desirably is applied to compositions that include less than 20 weight percent, preferably less than 5 weight percent, more preferably less than 1 weight percent water based on the total weight of the composition. Even more preferably, the compositions are anhydrous. As used herein, the term anhydrous means that a composition includes from 0 to 0.5, preferably from about 0 to about 0.2 weight percent water based on the total weight of the composition. To the extent that a composition includes undue water content, all or a portion of the water content can be removed and/or scavenged in advance of decolorization using any suitable drying and/or scavenging technique(s) before beginning the decolorizing treatment. Often, the water is removed from a amine composition when the lower molecular weight amines such as EDA and like are optionally separated from the composition prior to subjecting the composition to the decolorization method of the invention. EDA and other lower molecular weight amines (e.g., those including 1 to 3 amine moieties) are often obtained in high-quality via distillation without requiring any prior heat treatment. Consequently, the present invention is most advantageously applied to compositions including at least one amine that preferably includes four or more amine moieties.

As an overview, the decolorizing treatment applied to the amine(s) incorporates at least two steps to provide effective decolorization. In a first step, the discolored composition is heat treated in the presence of at least one suitable acid for a desired time period at one or more suitable temperatures. Without wishing to be bound, it is believed that the heat treatment conditions allow the acid to react with the color bodies, changing the molecular weight or otherwise modifying the species. The change(s) to the color bodies allow separation techniques such as distillation to more easily resolve the amine products in purer, low color form. The desired amine product(s) are thus much easier to separate from the modified color bodies, yielding decolorized product(s) more easily and effectively. Further, because of the low amount of the acid(s) used, less by-products are produced allowing the decolorization to be achieved more efficiently and in higher yield. With respect to a particular amine, such as L-TETA or the like, the product yield of that amine is the weight percent of the amine recovered with reduced color relative to the weight of that amine in the original composition. For example, if 90 grams of L-TETA with reduced color are recovered from an amine composition that originally included 100 grams of L-TETA, then the yield of L-TETA is 90% (90/100×100%). In a second step, separation techniques such as distillation are used to recover decolored compositions including the desired amines.

The present invention allows decolorized amines to be recovered in high yield with corresponding reductions in waste generation. For example, the present invention can convert highly colored compositions incorporating L-TETA (400 to 5000 APHA) into low color compositions (less than 50 APHA) at yields over 80%, even over 90% in a single treatment. If a greater degree of decolorization is desired, the decolorization may be carried out using a higher concentration of acid, a higher pre-treatment temperature, and/or a longer pre-treatment period. As other options for obtaining a greater degree of decolorization, more treatment cycles could be used to reduce color even more. However, a single cycle of treatment per the present invention reduces discoloration so dramatically that additional cycles of treatment are not needed. Additional cycles of treatment generally reduce yield of the desired product.

To begin the first stage of the treatment, one or more weak acids are added to the composition. As used herein, a weak acid refers to an acid having a pKa of greater than about 1, preferably greater than about 2, more preferably greater than about 3, even more preferably greater than about 4. As long as at least one weak acid is added to the composition, it is within the scope of the present invention to use one or more strong acid(s) (i.e., an acid having a pKa of less than 1, even less than −2, and even less than about −4) in combination with one or more weak acids. However, it is more preferred that strong acids, particularly strong acids including Cl, Br, and/or F, be excluded from the compositions for more optimum results. If a combination of weak acid(s) and strong acid(s) are used, it is desirable that at least 50 weight percent, preferably at least 75 weight percent, and more preferably at least 95 weight percent of the acids constitute weak acid(s) based on the total weight of the acids.

Weak acids, used singly or in combination, not only achieve substantial decolorization and are less corrosive when using surprisingly low levels of acid in a heat treatment, but these acids also achieve decolorization with substantially less by-product formation as compared to stronger acids with much lower pKa characteristics. Accordingly, at least one weak acid is used having a pKa of at least about 1, preferably at least about 2, even more preferably at least about 3, and even more preferably at least about 4.

A wide range of weak acids or their combinations may be used. Exemplary weak acids include organic acids, boric acid, and the like. Exemplary organic acids include carboxylic acids, dicarboxylic acids and anhydride precursors thereof such as acetic acid, acetic anhydride, oxalic acid, citric acid, maleic anhydride, maleic acid, formic acid, bor lactic acid, uric acid, glycolic acid, glyceric acid, barbituric acid, alloxanic acid, oxaloacetic acid, 3-butenoic acid, trans-crotonic acid, acetoacetic acid, 2 oxo-butanoic acid, methymalonic acid, succinic acid, malic acid, a-tartaric acid, meso tartaric acid, aspartic acid, butanoic acid, itaconic acid, mesaconic acid, 2-oxoglutaric acid, dimethylmalonic acid, methyl succinic acid, 2-methylbutanoic acid, 3-methylbutanoic acid, pentanoic acid, isocitric acid, o-phthalic acid, p-phthalic acid, m-phthalic acid, terephthalic acid, combinations of these, and the like. Glacial acetic acid having a pKa of 4.75 is preferred. Acetic acid is also very economical.

The acid(s) added to the composition may be aqueous or anhydrous. Anhydrous acids are preferred, as these reduce the need to remove as much water from the composition and reduce the potential loss of product(s) that may accompany the removal of water.

Any acid added to the composition may be liquid, gas or solid at room temperature, but desirably at least 50%, preferably at least 80%, even more preferably 100% of the acid is soluble at a temperature in the range from about 70° C. to about 200° C. when 0.1 to about 5 parts by weight of the acid(s) per about 100 parts by weight of amines in the composition. Thus, at least a substantial portion of the acid(s) is in a single phase with the composition being treated.

The amount of acid(s) added to the composition may vary over a wide range. The level of acid to be added depends on the concentration of the color-bodies in the amine composition or the temperature that can be achieved in the given equipment or the digestion time that could be allowed. If a high amount of acid is added, the decolorization proceeds faster and the decolorizing effect is high. However, if too much acid is added, the reaction of the acid with the composition may produce undue amounts of by-products including water, thereby reducing the efficiency and yield of the reaction. If too little acid(s) are added, a lesser degree of decolorization may be achieved than is desired or it takes longer to achieve the desired degree of decolorization. Balancing such concerns, the total amount(s) of acid(s) added to the composition in illustrative embodiments may be in the range from about 0.1 to about 5 parts by weight, preferably about 0.2 to about 3 parts by weight, more preferably from 0.2 to about 2 parts by weight, even more preferably from 0.3 to about 1.5 parts by weight and most preferably from 0.3 to about 1 part by weight of acid(s) per about 100 parts by weight of amines in the composition.

Although the amount of acid(s) added to the composition can vary over a wide range, it is desirable to minimize the acid used to accomplish the desired decolorization. The reaction between the acid and the composition produces one or more by-products, including water, in amounts corresponding to the amount of acid added. The formation of byproducts such as amides and imidazolines and the like from the reaction of the acid with the amine represents direct loss of the desired amine and it increases loss of desired product that accompanies removal of such byproducts such as in distillation. The presence of water may cause yield losses as well, as at least some desired product may be distilled along with water in a wet amine stream requiring further processing to recover some or all of the desired amines from the water. Consequently, minimizing the amount of acid added to the composition helps to increase the yield of low color amines while reducing the production of low value products and waste. Because the content of color bodies in the composition is relatively low, using correspondingly low amounts of acid would be effective to achieve the desired decolorization. It is best to ensure that the acid is mixed well with the amine composition to achieve best results from heat treatment.

The heat treatment generally is carried out for a suitable time period at one or more suitable temperatures effective to modify the color bodies in a manner that makes it easier to subsequently separate the desired amines from the color bodies. Without wishing to be bound, it is believed that the acid reacts with the color bodies to form species with higher molecular weights. The color of the heat treated composition often intensifies, but the color bodies are now in a form that makes it easier to more effectively separate the amines from the color bodies. When an objective is to reduce discoloring, it is counterintuitive that practicing a treatment that worsens the discoloration initially leads to more effective decolorization in the end. Advantageously, the acid is able to react with the composition without requiring any catalyst, although one or more catalysts could be used if desired to accelerate the results of the heat treatment.

The heat treatment may be carried out at one or more temperatures over a wide range. The rate of decolorization (modification of the color-bodies) increases with increasing temperature. If the temperature is too low, it may take longer than is practical for the characteristics of the composition to be altered as desired in a manner effective to facilitate subsequent recovery of amines with low color. If the temperature is too high, there may be an undue risk that one or more amines in the composition could be degraded. Often, the equipment, if pre-existing, may not be designed for a process operation at high temperatures. Balancing such concerns, the temperature(s) for heat treatment desirably is/are in the range from about 70° C. to about 200° C. The temperature is preferably at least 80° C. and more preferably at least 90° C. The heat treatment temperature is preferably less than about 180° C., more preferably less than about 160° C.

There is no particular restriction for the pressure during the heat-treatment. The heat-treatment can occur at atmospheric pressure or under vacuum, or even at a pressure greater than atmospheric pressure. However, the heat treatment desirably occurs in a protected environment so that the amine(s) are protected from the degrading effects of oxygen and/or other species that might be present in the atmosphere. The heat treatment generally occurs while mixing and/or moving the composition to help maintain a homogeneous reaction medium during the course of the heat treatment to achieve the best results.

The heat treatment generally occurs for a time sufficient to allow the acid to react with the composition to improve the ease by which the amines having low color can be separated. Generally, a reaction carried out at higher temperatures can occur in a shorter time than a reaction carried out at a lower temperature. Also, a heat treatment using a higher amount of acid tends to occur in a shorter time than a heat treatment with a lower amount of acid. In many embodiments, carrying out the heat treatment for a time in the range from about 3 minutes to about 150 hours, preferably from about 20 minutes to about 80 hours, more preferably from about 1 hour to about 50 hours would be suitable. In some embodiments, the progress of the pre-treatment may be monitored by sampling the composition, flash distilling the sample, and checking the color of the overhead product obtained from the distilled sample.

Use of the heat treatment provides many advantages. First, the decolorizing treatment is able to achieve greater amounts of color reduction per amount of acid with lower production of by-products. Further, faster throughput is achieved because the heat treatment allows substantial decolorization to occur in a single cycle of treatment. However, the present invention encompasses the option to perform multiple cycles of treatment if desired, but usually this is not required.

After the heat treatment is complete, a variety of techniques can be used to recover a decolorized composition comprising one or more amines. Examples of suitable recovery techniques include extraction, distillation, chromatography, combinations of these and the like. Distillation is preferred. Distillation allows recovery of a decolored composition stream including one or more amines with high yield and distillation is more economical.

Distillation desirably occurs under vacuum. In illustrative embodiments, pressures in the range of about 0.1 torr to about 150 torr, preferably about 1 torr to about 100 torr and more preferably about 1 torr to about 50 torr would be suitable. The temperature at bottom of the distillation apparatus generally corresponds to the amines composition and the pressure, but desirably distillation is carried out so that the bottom temperature is less than about 250° C., preferably less than about 200° C., more preferably less than about 180° C. and most preferably less than about 160° C. to minimize formation of byproducts and avoid undue risk of degradation of the amines.

Distillation generally yields a stream of low boiling materials and/or an aqueous stream obtained from the top of the column containing some amines, an anhydrous stream containing amines obtained from the top or side of the column, and a bottom stream of heavier components containing the modified color-bodies and the byproducts. The anhydrous stream is a source of low color amines. The other streams can be recovered for further processing, discarded, and/or the like. For example, the wet or the aqueous stream can be dried if desired and then used as is, further processed, and/or recycled back to the heat treatment and/or distillation steps. The bottom stream can be used as is, recycled back to the heat treatment or further processed.

The prior heat treatment dramatically increases the effectiveness of the distillation. Without wishing to be bound, it is believed that the heat treatment modifies the color bodies such as by changing the molecular weight of the color bodies. This in turn changes the boiling point of the color bodies, allowing the distillation to more easily resolve and separate the amines from the color bodies. In the absence of a heat treatment, the boiling point and volatility of the amines and color bodies are more similar and, hence, more difficult for distillation to resolve.

For example, in one experiment, a high color (APHA color of 800 or more) composition includes L-TETA. Glacial acetic acid is added to the composition and distillation proceeds without allowing the acid to pre-react with the composition in any significant way. Multiple cycles of acid addition and distillation are required to reduce the APHA color to less than 50. Further, the yield of low color L-TETA is less than 50% of the L-TETA contained in the starting composition. In contrast, by using a significant heat treatment prior to distillation, a single cycle of heat treatment using a lower amount of acid and distillation yields low color L-TETA at greater than 90% yield. At the same time, the production of undesired by-products are reduced by an order of magnitude relative to the case where significant heat treatment was not provided and yield of low color TETA was less than 50%.

The present invention will now be described in the context of an illustrative mode of practice. A composition containing one or more amines is provided. The composition is discolored and may have an APHA color of 200 or more, even 400 or more, and even from about 1000 to about 5000 APHA. Prior to heat treatment, one or more optional treatments may be applied to the composition to help make the heat treatment more effective. For example, if the composition contains a significant amount of low boiling amine components, the composition may be subjected to an initial distillation to remove the low boiling components as the low boiling components tend to distill in low color. Often, the color bodies remain in admixture with the higher molecular weight amine(s) after this initial distillation, and the compositions remain strongly colored. If the composition includes undue amounts of water, optionally the water content can be reduced to a more suit-able level. Water typically leaves with low boiling amines with distillation, so often a separate, dedicated water removal step is not needed to separate water from the desired higher amine product. Additionally, if only a portion of the amines in the composition constitute the desired product, the composition optionally can be subjected to a suitable separation technique in order to recover the desired products in more pure form with respect to the other amines that might be present. Alternatively, the entire admixture of amines can be treated in accordance with the present invention, after which a separation technique is used to recover the desired product in more pure form.

Glacial acetic acid is then added to the composition. Adding about 0.4 to about 1 parts by weight of the acid per about 100 parts by weight of amines would be suitable in more preferred embodiments. The resulting admixture is mixed well and heated at one or more desired temperatures to allow the composition to digest for a sufficient time to allow the subsequent distillation to more effectively resolve the amines from the color bodies. This may occur at a temperature in the range from about 70° C. to about 200° C. for a time period from 10 minutes to about 150 hours. Because the digestion time decreases with increasing temperature for a given degree of decolorization, it can be advantageous to use higher temperatures within the limits of the equipment capability in order to maximize throughput. After the heat treatment has progressed sufficiently, low color amines can be recovered by distilling the heat treated composition under vacuum. The pressure and temperature for the distillation are selected so that the temperature remains low enough to avoid undue degradation of the amines. Generally, keeping the bottom temperature of the column at about 200° C. or less would be suitable. Distillation desirably is carried out to minimize the fraction going to the bottom and the wet fraction going to the top while maintaining the purity of the amines stream obtained at the top or side of the column.

The present invention will now be described with reference to the following illustrative examples.

EXAMPLE 1

To 120 g of a high color composition (about 560 APHA) including 98.2 weight percent TETA and the balance being other amines including AEEA, TEPA, and the like (Sample 1) was added 1.2 g of glacial acetic acid. The mixture was mixed well. The mixture was subjected to a temperature of 92° C. under an inert atmosphere for a period of 48 hours. The color of the composition intensified after the heat treatment. The mixture was then transferred to a batch distillation apparatus having a 6 inch tall distillation column attached to a 3-neck round bottoms flask and provided with temperature control and vacuum. The distillation column did not contain any trays or packing. The distillation was carried out at a pressure of 8-10 ton and a temperature from 145° C. to 150° C. The top fraction of the distillation had a color of APHA 15.

EXAMPLE 2

An amine mixture (Sample 2) included 92.7 weight percent L-TETA, 6% TEPA, with the remainder being other polyethylene amines in small amounts. The mixture had a starting color of 4583 APHA. To 120 g of the mixture was added 1.2 g of glacial acetic acid. The mixture was mixed well. The mixture was subjected to a temperature of 92° C. under an inert atmosphere for a period of 48 hours. The mixture was then distilled as described in Example 1. The top fraction of the distillation had a color of APHA 28.

EXAMPLE 3

An amine mixture having the same composition as Sample 2 was heat treated for a shorter duration than was used in Example 2. To 120 g of the mixture was added 1.2 g of glacial acetic acid. The mixture was mixed well. The mixture was subjected to a temperature of 92° C. under an inert atmosphere for a period of 24 hours. The mixture was then distilled as described in Representative Example 1. The top fraction of the distillation had a color of APHA 150.

EXAMPLE 4

The following table provides additional examples that show how the decolorization result is a function of digestion time, temperature, and the amount of acid added. In each example, the resulting color is the color of the top fraction from distillation after digestion with acetic acid.

| Example Number | Material treated | Glacial Acetic acid concn. % | Digestion temp. C. | Digestion time, hrs | Result: Color in APHA |
|---|---|---|---|---|---|
| A | high color L-TETA | 3 | 92 | 50 | 13 |
| B | high color L-TETA | 0.5 | 92 | 48 | 63 |
| C | high color L-TETA | 0.5 | 92 | 72 | 41 |
| D | high color L-TETA | 1 | 92 | 48 | 6 |
| E | high color L-TETA | 0.5 | 81 | 72 | 114 |
| F | high color L-TETA | 0.5 | 81 | 144 | 25 |
| G | high color L-TETA | 1 | 81 | 48 | 62 |
| H | high color L-TETA + higher amines | 0.5 | 92 | 72 | 104 |
| I | high color L-TETA + higher amines | 1 | 92 | 72 | 37 |
| J | high color L-TETA + higher amines | 1 | 81 | 72 | 81 |
| K | high color L-TETA + higher amines | 1 | 101 | 72 | 33 |
| L | high color L-TETA + higher amines | 1 | 92 | 48 | 34 |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of reducing color of a composition including one or more amines, comprising the steps of:
   (a) providing the composition, wherein the composition has an initial color;
   (b) heat treating the composition in the presence of at least one weak acid for a period in the range from about 3 minutes to about 150 hours; wherein the weak acid has a pKa of at least about 1 and is selected from a carboxlic acid, a dicarboxylic acid, an anhydride of a dicarboxylic acid, and combinations of these; and
   (c) after heat treating, using at least a separation technique to recover at least a portion of the amines from the heat treated composition in a manner such that the recovered portion has less color relative to the initial color, wherein the separation technique is selected from distillation, extraction, chromatography, and combinations of these.

2. The method of claim 1, further comprising the step of monitoring the progress of the heat treatment said monitoring compressing sampling the heat treated composition, distilling the sample, and checking color of an overhead product obtained from distilling the sample.

3. The method of claim 1, wherein step (a) comprises providing a amine composition having a color in the range from about 400 APHA to about 5000 APHA.

4. The method of claim 1, wherein the amine composition comprises linear triethylenetetramine and/or a congener thereof.

5. The method of claim 1, wherein the at least one weak acid comprises acetic acid.

6. The method of claim 1, wherein the at least one weak acid comprises glacial acetic acid.

7. The method of claim 1, wherein the at least one weak acid has a pKa of at least about 2.

8. The method of claim 1, wherein the at least one weak acid has a pKa of at least about 4.

9. The method of claim 1, wherein heat treating occurs in the presence of an amount of weak acid(s) in the range from about 0.1 and 5 parts of the at least one weak acid per 100 parts of the amine composition.

10. The method of claim 1, wherein heat treating occurs for at least one hour.

11. The method of claim 1, wherein heat treating occurs for at least 24 hours.

12. The method of claim 1, wherein the heat treating occurs at a temperature in the range from about 70° C. to about 100° C.

13. The method of claim 1, wherein the heat treating occurs at a temperature in the range from about 100° C. to about 130° C.

14. The method of claim 1, wherein the heat treating occurs at a temperature in the range from about 130° C. to about 160° C.

15. The method of claim 1, wherein the heat treating occurs at a temperature in the range from about 160° C. to about 200° C.

16. The method of claim 1, wherein the color of the recovered amine composition is less than 150 API-IA.

17. The method of claim 1, wherein the color of the recovered amine composition is less than 50 APHA.

18. A method of reducing color of a composition including one or more amines, comprising the steps of:
(a) providing the composition, wherein the composition has an initial color;
(b) heat treating the composition in the presence of at least one weak acid for a period in the range from about 3 minutes to about 150 hours; wherein the weak acid comprises boric acid; and
(c) after heat treating, using at least a separation technique to recover at least a portion of the amines from the heat treated composition in a manner such that the recovered portion has less color relative to the initial color, wherein the separation technique is selected from distillation, extraction, chromatography, and combinations of these.

* * * * *

UNITED STATES PATENT AND TRADEMARK OFFICE
CERTIFICATE OF CORRECTION

Page 1 of 1

PATENT NO. : 8,853,459 B2
APPLICATION NO. : 13/876388
DATED : October 7, 2014
INVENTOR(S) : Anil J. Mehta It is certified that error appears in the above-identified patent and that said Letters Patent is hereby corrected as shown below:

In the Claims

Column 12:

Line 10, Claim 2 should be --monitoring the progress of the heat treatment,--

Line 11, Claim 2 "compressing" should be --comprising--

Signed and Sealed this
Twenty-eighth Day of July, 2015

Michelle K. Lee
*Director of the United States Patent and Trademark Office*